United States Patent [19]
Curley

[11] Patent Number: 4,985,123
[45] Date of Patent: Jan. 15, 1991

[54] IN SITU POLAROGRAPHIC SENSOR CALIBRATION

[75] Inventor: Michael G. Curley, Wellesley, Mass.

[73] Assignee: Massachusetts Institute of Technology, Cambridge, Mass.

[21] Appl. No.: 328,444

[22] Filed: Mar. 24, 1989

[51] Int. Cl.$^5$ ............................................. G01N 27/46
[52] U.S. Cl. ................................... 204/153.1; 73/1 R; 73/1 G; 204/401
[58] Field of Search ....................... 204/401, 1 P, 1 T; 73/1 G, 1 R

[56] References Cited

PUBLICATIONS

Winlove et al., "The Measurement of Oxygen Diffusivity and Concentration by Chronoamperometry Using Microelectrodes", J. Electroanal. Chem. 170: 293–304 (1984).
Hale et al., "Some Considerations of the Steady State and Transient Behavior of Membrane-Covered Dissolved Oxygen Detectors", J. Electroanal. Chem., 107: 281–294 (1980).
Hoffer et al., "Preliminary Study of On-Line Computation of Cardiac Output Using Indwelling Oxygen Catheters in Man", Fed. Proc. 31: Abs. 786 (1972).
Kunze et al., "Absolute PO$_2$ Measurements with Pt--Electrodes Aplying Polarizing Voltage Pulsing", Adv. in Exp. Med. and Biol. 37A: 35–43 (1973).

Primary Examiner—G. L. Kaplan
Attorney, Agent, or Firm—Fish & Richardson

[57] ABSTRACT

A coated polarographic sensor is calibrated by exposing the sensor to calibration media having known temperatures and species chemical potentials. The sensor is allowed to equilibrate with respect to the calibration media. After equilibration, the sensor is polarized with respect to a reference electrode and the resulting transient and steady state electrochemical currents are monitored. A transient calibration equation characterizing transient sensor performance is derived from the transient electrochemical current, and a quasi-steady state calibration equation characterizing steady state sensor performance is derived from the steady state electrochemical current. The transient current of the sensor is independent of the thermophysical properties of the species in the medium so that the transient current can serve to correct the quasi-steady state calibration equation for the sensor in situ. This in situ calibration of the steady state performance of the sensor allows for the application of thinner coatings of the sensor. The use of thinner coatings results in a sensor that responds more quickly to changes in chemical potential of the species. The sensor also registers a larger current at a given chemical potential thereby improving overall sensor performance.

8 Claims, 1 Drawing Sheet

IN SITU POLAROGRAPHIC SENSOR CALIBRATION

BACKGROUND OF THE INVENTION

The government has rights in this invention under a grant from the National Institutes of Health, NIH-5-R01-CA37235.

This invention relates to the calibration of polarographic sensors.

Polarographic sensors are used to determine the concentration or the thermodynamic chemical potential of many chemical species. In particular, the determination of the chemical potential of oxygen, or oxygen tension, is useful in the laboratory, in biomedicine, and in industrial process and environmental monitoring. See, *Polarography*, D. R. Crow et al. (1968), Methuen and Co. London and *Polarographic Oxygen Sensors: Its Theory of Operation and Its Application in Biology, Medicine and Technology*, I. Fatt (1982) Krieger, Malabar, Fla. Typically, a polarographic sensor is polarized in some fashion with respect to a non-polarizable reference electrode, often a silver/silver chloride electrode. The sensor is frequently fabricated from a noble metal, for example gold or platinum.

The polarographic sensor is placed in a medium, for example, living tissue, that may contain a chemical species whose concentration or thermodynamic chemical potential is to be measured. The species to be determined is oxidized or reduced on the sensor. The flow of current to or from the sensor, used to complete the electrochemical oxidation or reduction reaction, is indicative of the concentration of the species being oxidized or reduced. This electrochemical current is also a function of the thermophysical properties of the species in the medium, especially its solubility and diffusivity. See, "The Measurement of Oxygen Diffusivity and Concentration by Chronoamperometry Using Microelectrodes," Journal of Electroanalytical Chemistry, C. P. Winlove et al., Vol. 170, 1984, pp. 293–304. Because the electrochemical current can be a function of the thermophysical properties of the species in the medium, sensors are often coated with materials of known thermophysical properties so as to minimize the effect of variation of properties, such as solubility and diffusivity, on the measurement. The thermophysical properties of the sensor coating most often become known through calibration of the coated probe in media with known concentrations or chemical potentials of the species being measured.

Sensor coatings may consist of membrane encased electrolytic solutions covering the sensor and reference electrode, or of permeable solids and/or gels covering one or both sensors. See, "Some Considerations of the Steady State and Transient Behavior of Membrane-Covered Dissolved Oxygen Detectors," Journal of Electroanalytical Chemistry, J. M. Hale et al., Vol. 107, 1980, pp. 293–304; "Preliminary Study of on-line Computation of Cardiac Output Using Indwelling Oxygen Catheters in Man," J. L. Hoffer et al., Federation Proceedings, Vol. 31, 1972, p. 786; and "Absolute P02 Measurements with Pt-Electrodes Applying Polarizing Voltage Pulsing," K. Kunze et al., Advances in Experimental Medicine and Biology, Vol. 37A, 1973, pp. 35–43.

The sensor coatings render the measurement one of thermodynamic chemical potential of the species as opposed to concentration of the species in the medium. The dependence of the measurement on the thermophysical properties of the species in the medium is largely removed, but as the sensor is not directly contacting the medium, an effect on the species in the medium is not registered (measured) by the sensor for some time period after the effect occurs. The time period is determined by the coating thickness and thermophysical properties of the coating material. The time lag is also characterized by large transient current upon initial polarization of the sensor while excess amounts of the species in the coating are consumed. See, *Polarography*, 2nd Edition Interscience, I. M. Kolthoff et al., (1952) New York. This time lag is a characterizable property of the electrode.

In general, however, it is the long time (steady state) behavior of the current that has been used to determine the chemical potential of the species. In order to minimize the dependence of the measurement on the thermophysical properties of the species in the medium, coatings have been chosen which are relatively thick, and/or ones in which the species are relatively insoluble and/or slowly diffusive. Such coatings result in a slowly responsive sensor with a relatively low level signal.

SUMMARY OF THE INVENTION

The chemical potential of a species in a medium can be absolutely determined through the transient (short time) behavior of the electrochemical current of a coated polarographic sensor in contact with the medium. This short time, or transient, response of the sensor will be dependent only on the chemical potential of the species in the medium and on calibratable properties of the coated polarographic sensor. This absolute determination of the chemical potential can then be used to calibrate the long time (steady state) response of the sensor. If the steady state response is a function of undetermined thermophysical properties of the medium, these undetermined properties are accounted for in the calibration.

According to one aspect of the invention, a method for calibrating a coated polarographic sensor, the sensor is exposed to a calibration medium having known temperature and species chemical potentials. The sensor is allowed to equilibrate with respect to the calibration medium after which the sensor is polarized with respect to a reference electrode, also in contact with the calibration medium. The resulting transient and steady state electrochemical currents are monitored. A transient calibration equation characterizing transient sensor performance is derived from the transient electrochemical current, and a quasi-steady state calibration equation characterizing steady state sensor performance is derived from the steady state electrochemical current.

The sensor is next placed in a medium of known temperature whose species chemical potential is to be determined, and the sensor is allowed to equilibrate with respect to the medium. The sensor is polarized with respect to a reference electrode, and the resulting transient and steady state electrochemical currents are monitored. The transient electrochemical current and the transient calibration equation are used to accurately derive the chemical potential of the species. This chemical potential along with the steady state electrochemical current is used to adjust the quasi steady state calibration equation for subsequent continuous determination of the species chemical potential.

In a preferred embodiment of the calibration method, the sensor is exposed to calibration media having known species chemical potential, at a plurality of different temperatures to determine the temperature dependence of the transient and quasi-steady state calibration equations. During in situ use, sensor re-equilibration and repolarization may be repeated for further adjustment of the quasi-steady state calibration constant. The preferred species whose chemical potential is to be determined is oxygen and the preferred geometrical configuration of the sensor is a recessed plane. For a recessed plane sensor used in the determination of oxygen chemical potential (or oxygen tension, $P_0$), the transient calibration equation is $i=(At^{\frac{1}{2}})P_0$, where i is the transient current, A is the transient calibration constant and t is the time since sensor polarization; the quasi-steady state calibration equation is $i_{ss}=BP_0$, where $i_{ss}$ is the steady state current and B is the quasi-steady state calibration constant; and during measurement of oxygen tension, the factor $\eta$, used to adjust B, is defined by $i_{ss}=P_0B/(1+\eta)$.

According to another aspect of the invention, a method of determining the chemical potential of a species using a coated polarographic sensor involves calibrating the sensor using the calibration method described above, operating the sensor in a continuously polarized state, and using the adjusted quasi-steady state calibration constant and the steady state electrochemical current to determine the chemical potential of the species. Preferably, the method also involves monitoring changes in the chemical potential of the species over time.

The utilization of both a transient and a steady state calibration of a coated polarographic chemical potential sensor according to the invention offers significant advantages over the use of either one separately. Since the short time transient current of the electrode is absolutely independent of the thermophysical properties of the species in the medium, it can serve to correct the steady state calibration of the sensor. This in situ calibration of the steady state performance of the sensor allows for application of thinner coatings. The use of thinner coatings will in turn result in a sensor that responds more quickly to changes in chemical potential of the species and one that will register a larger current at a given chemical potential, improving overall sensor performance. In short, the need to use thick coatings to make the quasi-steady state sensor calibration independent of the medium, which results in a smaller polarographic current and a more slowly responsive sensor, is eliminated. Further, the use of the corrected quasi-steady state sensor calibration as a monitoring mode for the chemical potential of a species will provide an accurate determination of a chemical potential that is more easily performed and is continuous in time as opposed to the discrete determinations obtained from a repeated use of the transient calibrations. The use of the corrected steady state sensor calibration as a monitoring mode will also result in a sensor that is more rapidly responsive than one using a repeated transient calibration. This is a result of the relatively long time required for sensor/coating re-equilibration after depolarization. This re-equilibration time is a necessary step in the proper use of repeated transient measurements of thermodynamic chemical potential, and is not necessary when using quasi-steady state measurement protocol.

Other features and advantages of the invention will be apparent from the following description of the preferred embodiment thereof and from the claims.

DESCRIPTION OF THE PREFERRED EMBODIMENT

We first briefly describe the drawings.

DRAWINGS

Figure 1:
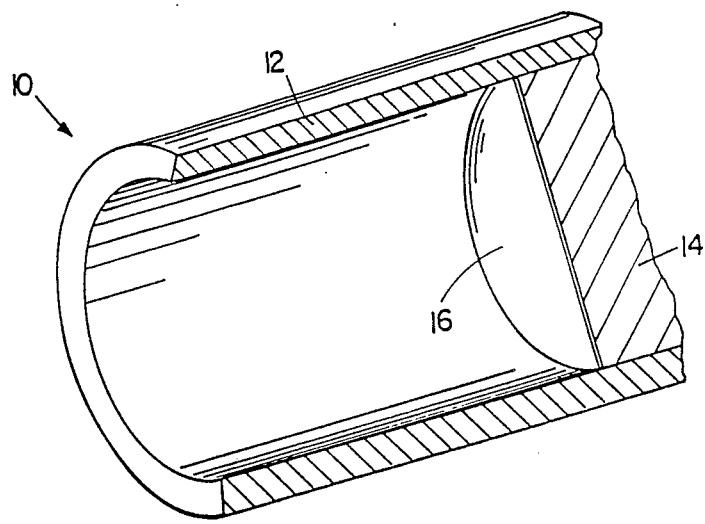
Figure 2:
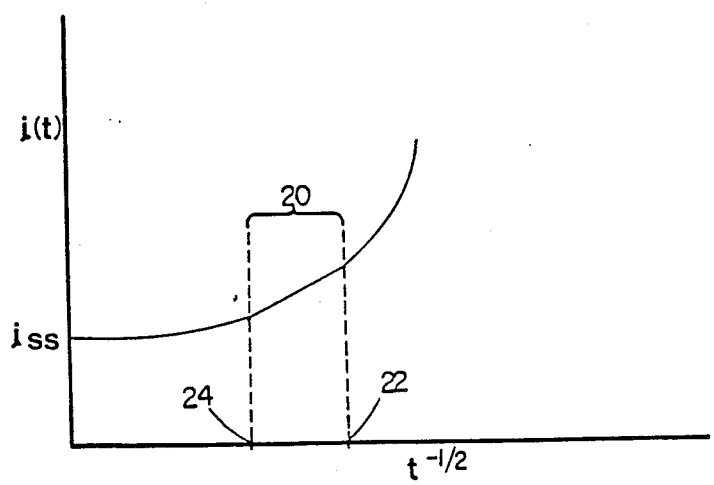

FIG. 1 is a perspective view, partially in section, of a coated polarographic sensor; and FIG. 2 is a graph of current plotted versus the inverse square root of time.

CALIBRATION METHOD

The method of the present invention will be described by way of example using a recessed polarographic oxygen sensor. This description is entirely exemplary and those skilled in the art will appreciate that the method can be used with various sensors for the determination of concentration or chemical potential of chemical species. For an oxygen sensor or electrode, the chemical potential (at a specific temperature) is a function of partial pressure of oxygen in the medium, known as oxygen tension. As such, in this preferred embodiment, the measurement of oxygen tension is described.

Polarographic sensors are generally constructed using one of a variety of methods. The sensors are precast, preformed, deposited, plated, or made in some other form in a variety of geometries, which include disk-shaped sensors, spherical or cylindrical sensors, rectangular plate sensors, and line sensors. These sensors can be surface mounted, or can be recessed into the sensor carrier (probe substrate). A disk-shaped, recessed noble metal sensor 10 is shown in FIG. 1. The sensor 10 includes a cylindrical casing 12 including a noble metal 14. A suitable noble metal is gold or platinum. The noble metal 14 is covered with a coating 16 which can be in a solid form, gelatinous form, or in a membrane covered liquid form. A reference electrode (not shown) can be proximally or remotely situated. If the reference electrode is remotely situated, the coating must be permeable to small ions as well as permeable to the species to be measured. If the reference electrode is proximal to the noble metal sensor, the coating need only be permeable to the species to be measured and to the species resulting from the electrochemical reaction.

To calibrate any electrochemical sensor, the sensor (or probe) is first placed in a medium of known temperature and species chemical potential. Because the determination of chemical potential is normally quite temperature sensitive, an accurate knowledge of temperature during calibration or during actual chemical potential determination is important. Calibration can be performed in any medium since the nature of the present invention is a method to account for medium to medium variations in probe calibration. It is prudent, however, to perform the calibration in a medium that is similar to the medium in which the sensor is to be ultimately used. As an example, for probes to be used in biological oxygen chemical potential (or oxygen tension) monitoring, physiologic saline solutions of known temperature and oxygen tension are often used as calibration media. Calibrations in media having three or more species chemical potentials and at several different temperatures are recommended.

The coated sensor is allowed to become equilibrated with the calibration medium and thereafter is polarized with respect to a reference electrode. The resulting electrochemical current is monitored including the relatively large transient current and the relatively small steady state current.

The very short time, transient current is independent of the medium thermophysical properties but is a function of the coating properties. The duration (time window) of this medium independent current is a function of the thickness and thermophysical properties of the coating. As this is normally a diffusion controlled process, this time window is proportional to the square of the thickness of the coating and to the diffusivity of the species in the coating. Beyond this time window, the concentration of the species being measured (oxidized or reduced) by the electrochemical reaction at the sensor surface is changed in the medium, and the properties of the species in the medium begin to affect the current. The temporal behavior of the short time, transient current is fit to qualitative or quantitative analytic models (calibration equations) describing the process. The fit of the data to the model results in constants of calibration characterizing the sensor performance during this short time window. Similarly, the long time (steady state) current measured by the sensor can be fit to a descriptive model of sensor performance resulting in calibration constants characterizing the performance of the sensor in quasi-steady state. The transient and quasi-steady state calibration constants are redetermined in the same calibration medium at a number of different temperatures and known species chemical potentials to determine their temperature dependence. The temperature dependence may be describable analytically, or it may need to be determined empirically.

The sensor is next placed in the medium whose species chemical potential is to be determined. The sensor is left in a passive (unpolarized) state for a length of time sufficient to allow chemical potential equilibrium between the coating and the medium to occur. This time period is a characterizable property of the sensor. After equilibrium has occurred, the sensor is polarized with respect to a reference electrode, and the current from the moment of sensor polarization forward is monitored as during the first stage of the calibration procedure. The temperature of the medium close to the polarographic sensor should be determined simultaneously with the polarization. Knowledge of the temperature is used to determine the appropriate transient and quasi-steady state calibration constants. The short time transient current data is fitted to the same analytic model within the same time window as during the first stage in the calibration protocol. Use of this fitting procedure and knowledge of the transient calibration constant at the medium temperature will result in a determination of the chemical potential of the species in the medium, which determination is independent of medium thermophysical properties. That is, since the transient calibration constant at the medium temperature is known from the first stage calibration protocol, oxygen tension ($P_0$) is computed from the transient current data.

The initial steady state current, $i_{ss}$, obtained after the short time window has passed, is then used to determine the validity of the quasi-steady state calibration constant, previously determined, under the existing conditions at the time of use. As the chemical potential of the species is known from the short time transient measurement, and the initial steady state current is known, the quasi-steady state calibration constant can be checked for accuracy and adjusted accordingly if found to be in error.

Use

An example using a recessed planar polarographic oxygen tension sensor will now be described. The sensor is first placed in a medium of known temperature and oxygen tension and left in an unpolarized state until oxygen tension equilibrium occurs between the recess and the medium. Next, the sensor is polarized at $-0.6$ to $-1.0$ volts with respect to a silver/silver chloride electrode. As is well known, a sensor with this geometrical configuration will register, for short times, a reduction current of oxygen that is proportional both to the inverse square root of time from the beginning of polarization (t) and to the oxygen tension ($P_0$) of the coating (and of the calibration medium). After the sensor/coating/medium system has reached steady state, the current should be proportional to the oxygen tension of the medium only. Written explicitly, the current i(t) for the recessed planar sensor system will act as follows:

Short time: $i = (At^{-\frac{1}{2}})P_0$

Long time: $i_{ss} = BP_0$ (For other geometries of the sensor, i will have a different functional dependence on t.) A and B are the constants of calibration that characterize the probe for short (transient) and long (steady state) times, respectively.

FIG. 2 shows a graph of current i(t) versus inverse square root of time elapsed since the polarization of the sensor. A time window 20 is the period of the medium independent current discussed above. For oxygen, this window extends from a time 22 of approximately a few milliseconds to 0.1 second to a time 24 of approximately 10 seconds. Note that in the time window 20, the curve is approximately linear. The transient calibration constant A is readily determined from the data in the time window 20. It is preferred that several points within the time window 20 be used to determine A and the results averaged to ameliorate the effects of inherent noise. The steady state current $i_{ss}$ is used to calculate the quasi-steady state calibration constant B. These calibration constants may be functions of temperature, so repeated determinations should be performed at different temperatures to establish the temperature dependency.

The recessed planar sensor is next placed in a medium of unknown oxygen tension and again allowed to equilibrate with the medium. The sensor is polarized at approximately $-0.8$ volts with respect to a silver/silver chloride electrode. The transient reduction current of oxygen at the cathode is monitored until a steady state current is recorded. The temperature of the medium is determined or estimated, and this temperature is in turn used to select the appropriate transient and quasi-steady state calibration constants, A and B, of the sensor. The transient current and transient calibration constant are used to accurately determine the oxygen tension $P_0$, using the same equation as before. An average of this value can be obtained over the valid temporal window to improve the signal to noise ratio of the measured current.

The initial steady state oxygen reduction current and the oxygen tension $P_0$ are used to obtain a correction to the quasi-steady state calibration constant B, if necessary. This correction can be written as a dimensionless factor $\eta$ given by $i_{ss}=P_0B/(1+\eta)$. The correction factor $\eta$ applied to the quasi-steady state calibration constant is a medium dependent property that accounts for any disturbance of the oxygen tension in the medium by the sensor. In general, it will be a function of the oxygen solubility and diffusivity of the medium, the temperature of the medium, the intimacy of sensor/medium contact, and of any relative motion between medium and sensor. The correction factor $\eta$ is then applied to the quasi-steady state calibration constant. Thereafter, the polarographic oxygen tension sensor is operated in a conventional, continuously polarized state to monitor changes in the chemical potential of the species in the medium. Sensor depolarization and repolarization after re-equilibration may be repeated as desired or as deemed necessary to monitor changes in the calibration correction factor $\eta$.

Other embodiments are within the following claims.

I claim:

1. Method for calibrating a coated polarographic sensor for the determination of species chemical potential comprising:
   (a) exposing the sensor to a calibration medium having known temperature and species chemical potential and allowing the sensor to equilibrate with respect to the calibration medium;
   (b) polarizing the sensor with respect to a reference electrode and monitoring the resulting transient and steady state electrochemical currents;
   (c) deriving a transient calibration constant characterizing transient sensor performance from the transient electrochemical current;
   (d) deriving a quasi-steady state calibration constant characterizing steady state sensor performance from the steady state electrochemical current;
   (e) placing the sensor in a medium of known temperature whose species chemical potential is to be determined and allowing the sensor to equilibrate with respect to the medium;
   (f) polarizing the sensor with respect to a reference electrode and monitoring the resulting transient and steady state electrochemical currents;
   (g) using the transient electrochemical current and the transient calibration constant to accurately derive the chemical potential of the species; and
   (h) using the chemical potential of the species derived in (g) and the steady state electrochemical current to adjust the quasi-steady state calibration constant for subsequent determination of species chemical potential.

2. The method of claim 1 wherein the sensor is exposed to calibration media having known species chemical potential, at a plurality of different temperatures to determine the temperature dependence of the transient and quasi-steady state calibration constants.

3. The method of claim 1 further, comprising repeating steps (e)–(h) for further adjustment of the quasi-steady state calibration constant.

4. The method of claim 1 wherein the species whose chemical potential is to be determined is oxygen.

5. The method of claim 1 wherein the sensor is in a recessed plane geometrical configuration.

6. The method of claim 5 wherein the species is oxygen and a property that determines the chemical potential is oxygen tension $P_0$ and wherein the relationship among the transient electrochemical current (i), the transient calibration constant (A) and the species chemical potential (or oxygen tension $P_0$) is defined by the equation $i=(At^{-\frac{1}{2}})P_0$, where t is equal to the time since polarization of the sensor;

the relationship among the steady state electrochemical current ($i_{ss}$), the quasi-steady state calibration constant (B), and the species chemical potential (oxygen tension or $P_0$) is defined by the equation $i_{ss}=BP_0$; and the factor $\eta$ used to adjust the quasi-steady state calibration constant (B) is defined by the equation $i_{ss}=P_0B/(1+\eta)$.

7. A method of determining the chemical potential of a species using a coated polarographic sensor comprising:

calibrating the sensor using the method of claim 1, operating the sensor in a continuously polarized state, and using the adjusted quasi-steady state calibration constant and the steady state electrochemical current to determine the chemical potential of the species.

8. The method of claim 7 further comprising monitoring changes in the chemical potential of the species over time.

* * * * *